United States Patent [19]

Posey-Dowty et al.

[11] Patent Number: 5,106,614

[45] Date of Patent: * Apr. 21, 1992

[54] BONE CEMENT FOR SUSTAINED RELEASE OF SUBSTANCES

[75] Inventors: Jessica Posey-Dowty, Kingsport, Tenn.; Paul A. Higham, Ringwood, N.J.; Nestor A. Arroyo, East Windsor, N.J.; Casper F. Stark, Pompton Lakes, N.J.

[73] Assignee: Pfizer Hospital Products Group, Inc., New York, N.Y.

[ * ] Notice: The portion of the term of this patent subsequent to Feb. 13, 2007 has been disclaimed.

[21] Appl. No.: 452,939

[22] Filed: Dec. 18, 1989

Related U.S. Application Data

[63] Continuation-in-part of Ser. No. 79,627, Jul. 30, 1987, Pat. No. 4,900,546.

[51] Int. Cl.$^5$ .............. A61K 31/74; A61K 31/78; A61F 2/00
[52] U.S. Cl. .................. 514/210; 424/423; 424/78.31; 623/16
[58] Field of Search ............ 424/78, 81, 423; 626/16

[56] References Cited

U.S. PATENT DOCUMENTS

| | | | |
|---|---|---|---|
| 3,882,858 | 5/1975 | Klemm | 128/92 |
| 4,059,684 | 11/1977 | Gross et al. | 424/81 |
| 4,373,217 | 2/1983 | Draenert | 523/116 |
| 4,588,583 | 5/1986 | Pietsch et al. | 424/81 |
| 4,900,546 | 2/1990 | Posey-Dowty et al. | 424/81 |

FOREIGN PATENT DOCUMENTS 1532318 11/1978 United Kingdom .

OTHER PUBLICATIONS

CA 91:83539k "Cephalosporins in Bone Cement", Hughes et al. (1979) J Bone & Joint Surgery.
CA: 93:53943, "Stability of Cephalothin, Ceformandole etc." Garcie Iglenices (1980).
92:169177y Studies in Antibotic Bone Cement Mixtures; Wahlij (1980).
Pichnell et al., "Antibacterial Activity of Antibiotic in Acrylic Bone Cement"; J. of Bone & Joint Surgery, p. 302 (1977).
Levin, "Effectiveness of Various Antibiotics in MMA" J. Bones Joint Surgery, p. 234 (1975).
Marks, "Antibotic Impregnated Acrylic Bone Cement" J Bones Joint Surgery, p. 358 (1976).

Primary Examiner—Lester L. Lee
Attorney, Agent, or Firm—Peter C. Richardson; Lawrence C. Akers; Raymond W. Augustin

[57] ABSTRACT

A bone cement is disclosed wherein the liquid component contains a therapeutic or diagnostic substance in combination with an emulsifying agent for said substance.

7 Claims, 2 Drawing Sheets

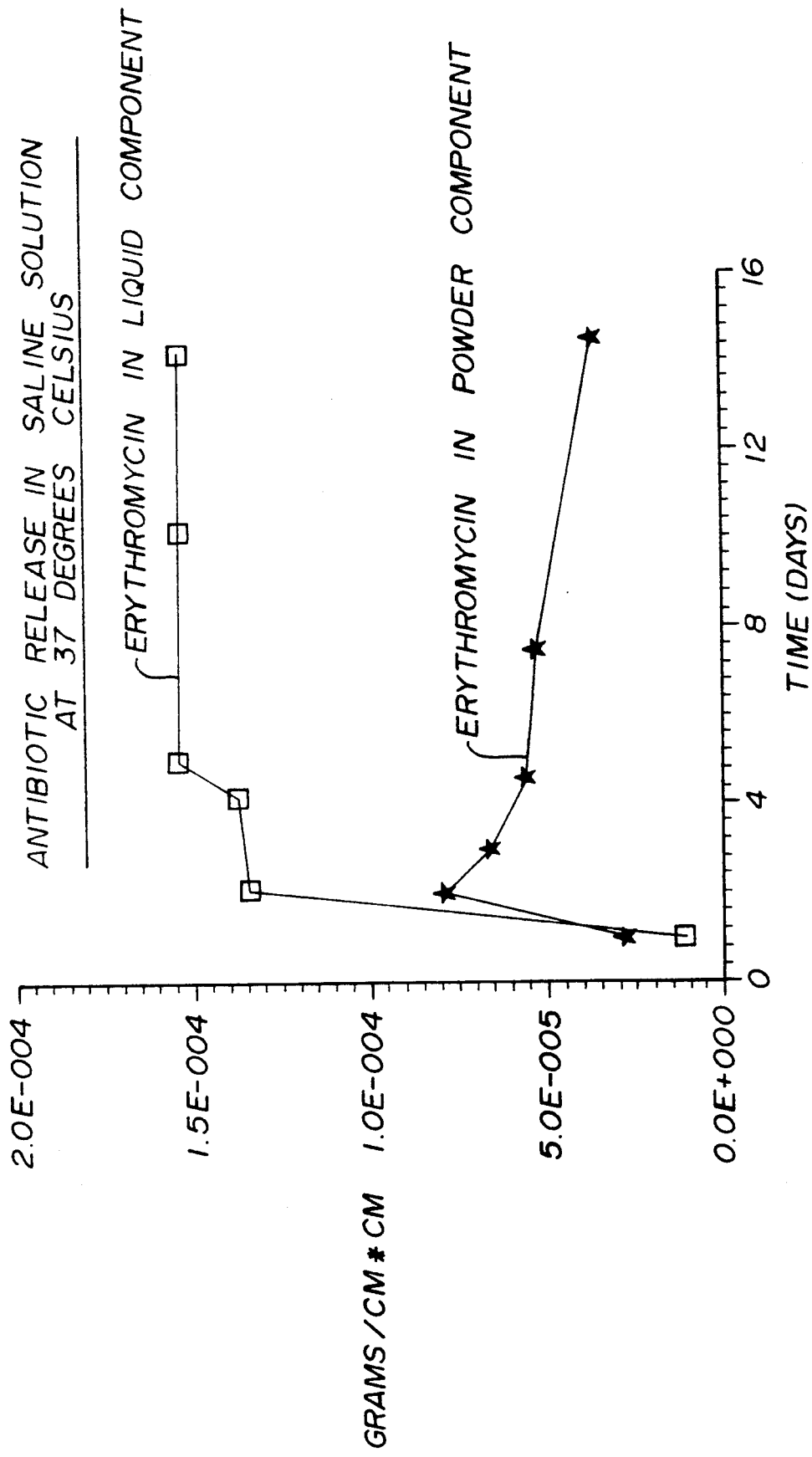

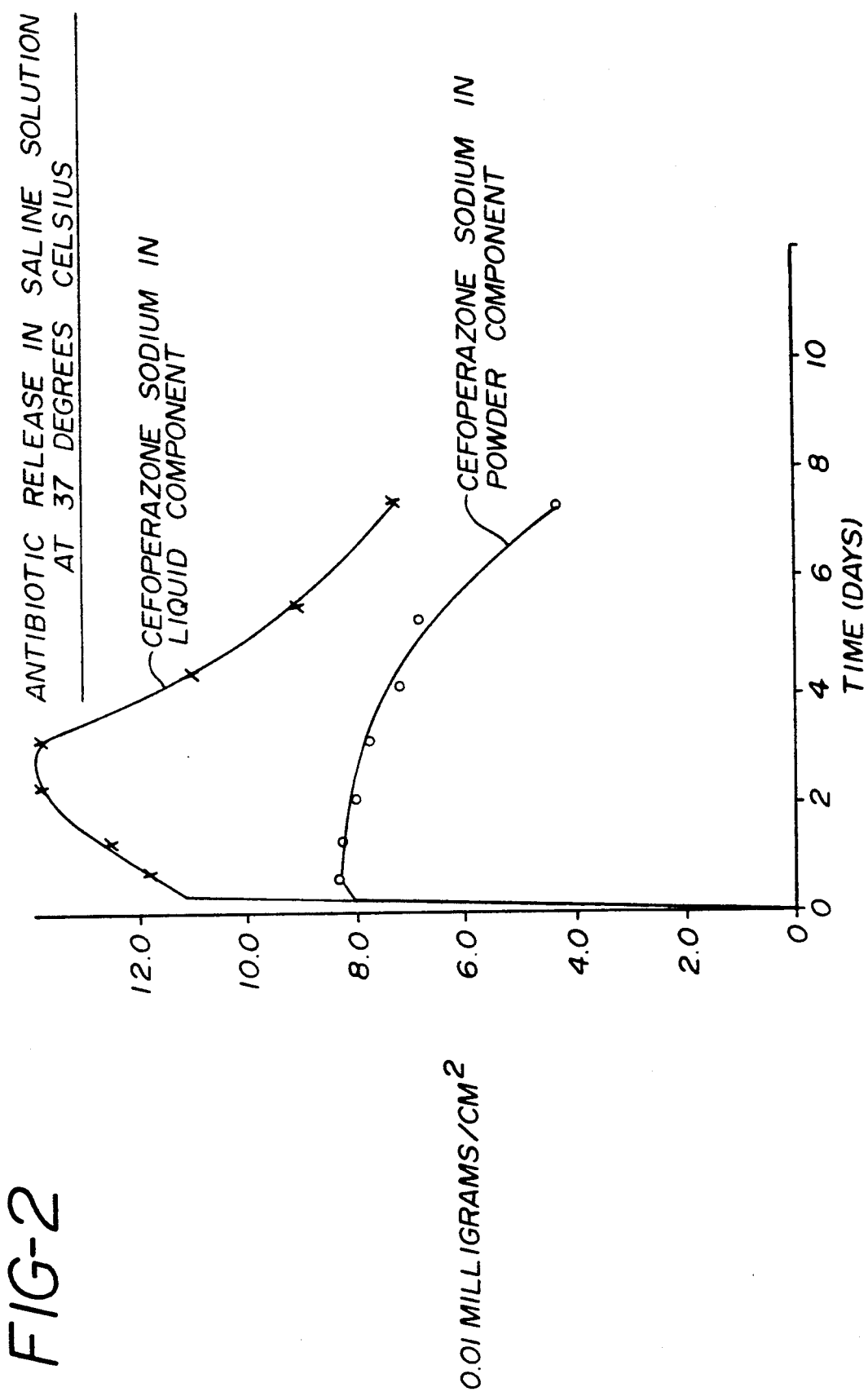

BONE CEMENT FOR SUSTAINED RELEASE OF SUBSTANCES

This is a continuation in part of application Ser. No. 079,627, filed Jul. 30, 1987, U.S. Pat. No. 4,900,546.

BACKGROUND OF THE INVENTION

The present invention relates to a bone cement. More particularly, the present invention relates to a bone cement wherein a diagnostic or therapeutic agent is incorporated in the liquid component with the agent being incorporated by the use of an emulsifying agent.

Bone cements find wide usage in a variety of applications. For instance, they are used for cementing implants in place, for the anchoring of endoprostheses of the joints, in the treatment of skull defects, and for the performance of spinal fusion.

Typically, these bone cements are made by mixing together a powdered homopolymer or copolymer of methylmethacrylate and a suitable liquid monomer, usually methylmethacrylate in the presence of a catalyst system. Additionally, the bone cement may also contain x-ray contrast agents, such as barium sulfate or zirconium dioxide, or dyes for the identification of the bone cement in the body.

In usage, a doughy mixture is prepared from the two components which is then placed in the body and allowed to set in situ due to polymerization of the monomer. Polymerization of the monomer can be accelerated by the presence of a redox catalyst system, usually an organic peroxy compound, such as dibenzoyl peroxide, plus a reducing component, such as p-toluidine.

The placement of a foreign object, such as the bone cement or cemented prosthesis, requires that prophylactic measures be taken to guard against infection at the boundary surfaces found between the bone cement and bone, and/or between the bone, bone cement, and prosthesis. Such prophylactic measures have generally involved the addition of antibiotics to the bone cement.

For instance, in U.S. Pat. No. 4,059,684, the antibiotics which are added to the bone cement are the hydrohalides or sulfates of gentamicin in combination with sodium chloride, potassium chloride, sodium bromide or potassium bromide. In this patent, the antibiotic can be incorporated into either the powdered polymer or copolymer or the liquid monomer. No mention is made of the addition of an emulsifying agent to incorporate the antibiotic into the liquid monomer.

Other antibiotics which have been added to bone cement include penicillin and tetracycline, which in most instances, are added to the powdered polymer or copolymer.

In United Kingdom Patent No. 1,532,318, the methylmethacrylate liquid monomer is present as an emulsion in water. No mention is made of the incorporation of antibiotics into this monomer.

In all situations wherein an antibiotic is added to a bone cement, the initial release is in a relatively high concentration to assure its bactericidal and bacteriostatic action. After this initial release, a diminution of the concentration takes place with the release rate, which is now lower, remaining relatively constant over a longer period of time. The net result is that even though the antibiotic release is sustained, the active concentration of the antibiotic is low. Thus, early infections may be prevented but later infections may not be reliably prevented or combatted. As is known, increasing the concentration of antibiotic may impair the mechanical strength of the bone cement so there remains a need for a bone cement from which the antibiotic will be released at both a sustained rate and at a high concentration.

BRIEF DESCRIPTION OF THE DRAWINGS

FIG. 1 is a graph showing the concentration of released erythromycin over a sustained time period from a bone cement of the present invention.

FIG. 2 is a graph showing the concentration of released active cefoperazone over a sustained period of time from a bone cement of the present invention.

SUMMARY OF THE INVENTION

The present invention is directed to a bone cement comprising the combination of components A and B wherein:

Component A comprises a powdered polymer or copolymer of an acrylic ester and,

Component B comprises a liquid monomer of an acrylic ester containing (a) a diagnostic or therapeutic substance, and (b) an emulsifying agent for said diagnostic or therapeutic substance, whereby the incorporation of said diagnostic or therapeutic substance in the bone cement composition is substantially in component B.

Preferred powdered polymers or copolymers of acrylic esters include methacrylates, methylmethacrylates and copolymers of methylmethacrylate and styrene.

Preferred liquid monomers of acrylic esters include methylmethacrylates.

Prepared substances include therapeutic substances such as erythromycin, cefoperazone, gentamicin, or colistin, combinations thereof, or pharmaceutically acceptable salts thereof. Most preferred are pharmaceutically acceptable salts of erythromycin.

Preferred emulsifying agents include sorbitan mono oleate polyoxyethylene and sodium dihexyl sulfosuccinate.

Another aspect of the present invention is the liquid monomer of an acrylic ester containing the diagnostic or therapeutic substance and an emulsifying agent for said substance.

DETAILED DESCRIPTION OF THE INVENTION

The present invention provides a composition for the preparation of a bone cement from which, e.g., an antibiotic will be released in a sustained high concentration.

The first component of the composition comprises a powdered polymer or copolymer of an acrylic ester. By the term "polymer or copolymer of an acrylic ester" is meant a polymer of an acrylate, e.g. a methacrylate, polymethylmethacrylate etc., as well as copolymers of the above compounds with non-acrylates, for example, such as methyl methacrylate-styrene copolymers. In addition, the powder component may contain an x-ray contrast agent such as barium sulfate or zirconium dioxide. If present, these x-ray contrast agents, especially barium sulfate, are added in the amount of about 5 to 15 weight percent with respect to the powdered polymer or copolymer. A catalyst, typically benzoyl peroxide, may also be incorporated in the powdered polymer or copolymer, in which case a reducing agent, for example, dimethyl p-toluidine, would be incorporated in the liquid monomer. Alternatively, the powdered polymer or copolymer may contain a reducing agent, in which case a peroxide catalyst would be incorporated in the liquid monomer.

The second component of the bone cement composition comprises a liquid monomer of an acrylic ester containing (a) a diagnostic or therapeutic substance and (b) an emulsifying agent for said diagnostic or therapeutic substance. This results in the incorporation of the diagnostic or therapeutic substance present in the bone cement composition being substantially in component B. By "substantially" is meant that at least 75% of the diagnostic or therapeutic substance in the composition is in component B. Higher ranges can also be used with as much as 80-90% of the diagnostic or therapeutic substance being incorporated in component B. In a preferred case, 100 percent of the diagnostic or therapeutic agent in the bone cement composition can be incorporated in component B. A preferred liquid monomer of an acrylic ester is methylmethacrylate. In the present invention, it has surprisingly been found that incorporation of the diagnostic or therapeutic agent into the liquid monomer by means of the emulsifying agent leads to a high sustained concentration of the diagnostic or therapeutic substance over time. The remainder of the specification will discuss the increased concentration of therapeutic substances, especially antibiotics, but is is to be understood that the discussion applies equally well to diagnostic substances, such as radioactive tracers, etc., as well as other classes of therapeutic substances such as anti-cancer drugs, anti-inflammatory drugs, immunostimulants, immunosuppressants, osteogenesis promotors, etc.

In the present invention, a major proportion of the antibiotic is preferably incorporated in the liquid monomer by means of an emulsifying agent. This results in a number of advantages over the previously known methods in which the antibiotics were compounded with the powder component of the cement. One problem associated with this method was the requirement that there be proper mixing of the therapeutic agent with the powder component with homogeneous dispersion of the antibiotic and elimination of aggregates. Such results were not always achieved. Other requirements for the effective release of the therapeutic substance into the liquid monomer; namely the requirement of a large surface area for the diffusion of water from the surrounding tissues into the cement mantle and the requirement that the substance contained in the cement mantle be soluble in the liquid containing the substance, are eliminated. The liquid which does get transported out of the cement mantle into the surrounding tissue contains the desired substance. Thus, a number of advantages are apparent.

Examples of antibiotics which can be incorporated into the liquid monomer are erythromycin, gentamicin, cefoperazone, colistin, penicillin, Terramycin, Aureomycin, Vebramycin, etc. Especially preferred antibiotics are erythromycin, gentamicin and colistin. The concentration of antibiotic which may be incorporated into the liquid monomer ranges from about 0.03 to about 8.0 weight percent, based on the liquid monomer. Of course, those skilled in the art to which this invention applies will recognize that, depending upon the activity of the antibiotic, higher or lower ranges can also be used.

In the present invention, the antibiotic, or other diagnostic or therapeutic agent, is incorporated into the liquid monomer by means of a emulsifying agent. An especially preferred emulsifying agent is sorbitan monooleate polyoxyethylene, also known as Tween 80. Another preferred emulsifying agent is sodium dihexyl sulfosuccinate. Other emulsifying agents which can be used in the present invention are polyoxyethylensorbitanmonopalmitate, polyoxyethylensorbitanmonostearate and polyoxyethylenesorbitanmonooleate. In addition to stabilizing the therapeutic substance in the liquid monomer, the emulsifying agent also possibly serves to dissipate the heat formed during the exothermic polymerization of the monomer. In the present invention, the emulsifying agent is present in an amount ranging from about 0.1 to about 10.0 weight percent, based on the liquid monomer.

In formulating the liquid monomer/therapeutic substance component of the present invention, the order of mixing of the ingredients is not critical. For instance, the antibiotic, for example, may be dissolved in water, if it is water soluble, and the emulsifying agent can be added to the dissolved antibiotic. The emulsified antibiotic can then be added to the liquid monomer. If the antibiotic is soluble in the liquid monomer, the antibiotic may be added to the monomer containing the emulsifying agent or the antibiotic mixed with the emulsifying agent may be added to the liquid monomer.

While the invention has been described with relation to a bone cement comprising the combination of the powdered polymer or copolymer and the liquid monomer containing the diagnostic or therapeutic substance plus the emulsifying agent, it will be apparent that the liquid monomer itself containing the emulsifier and diagnostic or therapeutic substance is also contemplated as being another aspect of the present invention. This liquid monomer/therapeutic or diagnostic substance/emulsifying agent composition can be used as a foreproduct for bone cement. Accordingly, such composition also forms a part of the present invention.

The present invention is illustrated by the following examples, which are not to be construed as limiting the invention, the scope of which is to be determined by the appended claims.

Bone cements of the invention are made by adding the following indicated liquid components to a powder component containing a radiopacifier. The cement is hand-mixed in a conventional manner for known bone cement. The following examples give the method of preparing the liquid component to be mixed with the powdered component.

EXAMPLE 1

The liquid component was prepared by mixing the following ingredients in the order given. The components were mixed in a resealable polyethylene container until all were evenly dispersed.

1. 3.655 g erythromycin gluceptate
2. 17.8 g water
3. 1.8 ml Tween 80
4. 100 ml of Methyl methacrylate monomer (97.4% v/v), (containing also 2.5 ml N, N-dimethyl-para-toluidine (2.6% v/v) and 75±15 ppm hydroquinone).

One fifth of this mixture was added per dose of the powder component, 40 g, (containing 6.0 g Polymethyl methacrylate (15% w/w), 30.0 g of Methyl methacrylate-styrene-copolymer (75% w/w) and 4.0 g Barium Sulfate U.S.P. (10% w/w)) and hand-mixed to form the bone cement.

EXAMPLE 2

Another liquid component was prepared by adding the following ingredients in the order given in the same way as Example 1.
1. 1.5 g erythromycin gluceptate
2. 7.08 g water
3. 0.7 ml Tween-80
4. 40.0 ml Methyl methacrylate (97.4% v/v Methyl methacrylate, 2.6% v/v N, N-dimethyl-para-toluidine, 75±15 ppm hydroquinone).

Two doses of the powder component (80 g) containing 12.0 g Polymethyl methacrylate (15% w/w), 60.0 g Methyl methacrylate-styrene-copolymer (75% w/w), 8 g Barium Sulfate U.S.P. (10% w/w)) were hand-mixed with the liquid to form the cement.

EXAMPLE 3

Another liquid component was prepared by adding the following ingredients in the order given.
1. 0.731 g erythromycin gluceptate
2. 2.07 g water
3. 3.2 g Aerosol MA-80
4. 40.0 ml Methyl methacrylate (containing 97.4% v/v Methyl methacrylate, 2.6% v/v N, N-dimethyl-paratoluidine(2.6%) and 75±15 ppm of hydroquinone).
5. 0.731 g erythromycin gluceptate Two doses (80 g) of powder component containing 15% w/w Polymethyl methacrylate w/w, 75% w/w Methyl methacrylate-Styrene-copolymer and 10% Barium Sulfate U.S.P.) were hand-mixed with the above liquid component to form the cement.

EXAMPLE 4

The following ingredients were mixed in the order given.
1. 1.670 g gentamicin sulfate
2. 7.440 g water
3. 0.753 g Tween-80
4. 40.0 ml Methyl methacrylate (containing 97.4 v/v Methyl methacrylate, 2.6% v/v N, N-dimethyl-paratoluidine, and 75±15 ppm hydroquinone)
5. 2.11 g liquid component in Example 1

The liquid component was added to the powder component, 80 g, (containing 15% w/w Polymethyl methacrylate, 75% w/w Methyl methacrylate-Styrene-copolymer and 10% w/w Barium Sulfate, U.S.P.) and hand-mixed to form the cement.

EXAMPLE 5

Another liquid component was prepared by adding the following ingredients in the order given in the same way as Example 1.
1. 0.500 g of Cefoperazone sodium
2. 4.0 g water
3. 0.4 g Tween 80
4. 10.0 ml of Methyl Methacrylate monomer (97.4% v/v) containing also 2.5 ml N, N-dimethyl - paratoluidine (2.6% v/v) and 75±15 ppm hydroquinone.

One dose of the powder component (40 g) containing 6.0 g Polymethyl methacrylate (15% w/w) 30 g of Methyl Methacrylate-styrene - Polymer (75% w/w) and 4.0 g Barium Sulphate USP (10% w/w) and hand mix to form cement.

We claim:

1. A bone cement composition comprising the combination of components A and B wherein:
   Component A comprises a powdered polymer or copolymer of an acrylic ester and, component B comprises a liquid monomer of an acrylic ester containing (a) cefoperazone or pharmaceutically acceptable salts thereof, an emulsifying agent for the cefoperazone, or pharmaceutically acceptable salts thereof, whereby the incorporation of cefoperazone or pharmaceutically acceptable salts thereof, is substantially in component B.

2. The bone cement of claim 1 wherein component A is polymethyl methacrylate.

3. The bone cement of claim 1 wherein component A is a copolymer of methylmethacrylate and styrene.

4. The bone cement of claim 1 wherein component B is methylmethacrylate.

5. The bone cement of claim 1 wherein said emulsifying agent is sorbitan mono-oleate polyoxyethylene.

6. The bone cement of claim 1 wherein said emulsifying agent is sodium dihexyl sulfosuccinate.

7. A liquid monomer of an acrylic ester containing (a) cefoperazone, or pharmaceutically acceptable salts thereof and (b) an emulsifying agent for the cefoperazone or pharmaceutically acceptable salts thereof.

* * * * *